United States Patent [19]
Schroeppel et al.

[11] Patent Number: 5,769,881
[45] Date of Patent: Jun. 23, 1998

[54] ENDOCARDIAL LEAD WITH MULTIPLE BRANCHES

[75] Inventors: Edward A. Schroeppel; Paul R. Spehr, both of Lake Jackson, Tex.

[73] Assignee: Sulzer Intermedics Inc., Angleton, Tex.

[21] Appl. No.: 862,104

[22] Filed: May 22, 1997

[51] Int. Cl.⁶ ..................................................... A61N 1/05
[52] U.S. Cl. .......................................... 607/123; 600/375
[58] Field of Search .................................... 607/122, 123, 607/126–128, 130; 600/373–375, 377, 381; 604/264, 280, 284

[56] References Cited

U.S. PATENT DOCUMENTS

| | | |
|---|---|---|
| 3,902,501 | 9/1975 | Citron et al. . |
| 3,939,843 | 2/1976 | Smyth . |
| 3,943,936 | 3/1976 | Rasor et al. . |
| 4,233,992 | 11/1980 | Bisping . |
| 4,378,023 | 3/1983 | Trabucco . |
| 4,567,901 | 2/1986 | Harris ....................................... 607/123 |
| 4,643,201 | 2/1987 | Stokes ...................................... 607/123 |
| 4,721,118 | 1/1988 | Harris . |
| 4,858,623 | 8/1989 | Bradshaw et al. . |
| 5,115,818 | 5/1992 | Holleman et al. . |
| 5,144,960 | 9/1992 | Mehra et al. ............................. 607/123 |
| 5,179,962 | 1/1993 | Dutcher et al. . |
| 5,257,634 | 11/1993 | Kroll ........................................ 607/122 |
| 5,314,462 | 5/1994 | Heil et al. ................................ 607/128 |
| 5,385,579 | 1/1995 | Helland .................................... 607/130 |
| 5,476,500 | 12/1995 | Fain et al. ................................ 607/126 |
| 5,571,162 | 11/1996 | Lin ........................................... 607/122 |
| 5,601,614 | 2/1997 | Ekwall ..................................... 607/25 |

FOREIGN PATENT DOCUMENTS

| | | |
|---|---|---|
| 0 004 967A2 | 4/1979 | European Pat. Off. . |
| 3529578 A1 | 2/1987 | Germany . |

OTHER PUBLICATIONS

Kevin Morgan et al., A New Single Pass DDD Lead, all pages, 8 May 1997.

Peter P. Karpawich, "Septal Pacing: A New Approach to Improve Paced Left Ventricular Function" European Journal of Cardiac Pacing & Electrophysiology, vol. 6, No. 1, p. 143, Jun. 1996.

R. McVenes, "What Tools Do We need For Multi Site Stimulation?"; European Journal of Cardiac Pacing Electrophysiology, vol. 6, No. 1, p. 145, Jun. 1996.

Primary Examiner—Jeffrey R. Jastrzab
Attorney, Agent, or Firm—John R. Merkling; Timothy M. Honeycutt

[57] ABSTRACT

A lead assembly includes a proximal end that has a connector for electrical connection to a cardiac stimulator, such as a pacemaker, a cardioverter/defibrillator, or a sensing instrument. The lead assembly includes an elongated proximal tubular portion that extends distally from the connector. The distal end of the proximal tubular portion is provided with a branch assembly that is joined distally to two elongated distal lead branches. The distal branches are provided, respectively, with lead tips that each function as electrodes for transferring electrical signals from and/or to the myocardium. The branch assembly includes structure for enabling a surgeon to selectively manipulate the distal branches using a single stylet passed through a single lumen in the proximal tubular portion.

16 Claims, 5 Drawing Sheets

ENDOCARDIAL LEAD WITH MULTIPLE BRANCHES

BACKGROUND OF THE INVENTION

1. Field of the Invention

This invention relates generally to implantable cardiac stimulation leads. This invention relates more particularly to multiple branch endocardial leads for cardiac stimulation.

2. Description of the Related Art

Early experimentation in dual-chamber pacing began several years ago and involved pacing in both the right atrium and the right ventricle. Early lead systems for dual-chamber pacing requiring two separate elongate implanted side-by-side within the particular introduction vein, such as the subclavian vein, are still almost universally in use. Later designs proposed replacing the separate longitudinal leads with a lead that incorporated multiple distal branches coupled to a single tubular proximal section that housed side-by-side apertures, one for each of the distal branches. These conventional multiple distal branch leads typically require either a bifurcated proximal connector the requires multiple connection ports on the cardiac stimulator or an in-line proximal connector that has side-by-side stylet openings.

There are several disadvantages associated with the conventional multiple distal branch leads. As noted above, the bifurcated proximal connector design requires either a multiple port cardiac stimulator or a special adapter to converge the multiple connectors to a single port. In addition, the bifurcated proximal connector is necessarily more bulky and invasive than a single connector. An in-line connector with two stylet openings is less invasive than the bifurcated proximal connector design and does not require a dual port adapter for connection to the cardiac stimulator. However, the dual stylet in-line connector, like the bifurcated proximal connector design, still requires side-by-side lumens extending from the connector to the division between the individual distal branches. Furthermore, the dual stylet connector is difficult to construct and label so that surgeons may readily identify and match a particular stylet opening with a particular distal branch.

The present invention is directed to overcoming or reducing one or more of the foregoing disadvantages.

SUMMARY OF THE INVENTION

In accordance with one aspect of the present invention, a branch assembly for a cardiac lead that has a proximal tubular portion, a first distal branch, and a second distal branch that are adapted to be spatially manipulated by a stylet that has a key provided. The branch assembly includes a housing that has a proximal end adapted to be coupled to the proximal tubular portion of the lead. The housing has a first flange that is adapted to be coupled to the first distal branch and a second flange that is adapted to be coupled to the second distal branch. The housing includes an inlet passage that has the same general cross-section as the stylet whereby the stylet may be received in a first preselected angular orientation, and a chamber that extends from the inlet passage to the first and second flanges. A diverter member is coupled to the housing and is disposed in the chamber. The diverter member has a narrowed edge projecting proximally within the chamber whereby the stylet may be selectively wedged to either the first branch or the second branch when the stylet is thrust against the diverter member.

In another aspect of the present invention, an assembly for spatially manipulating the branches of a multiple branch cardiac lead that has a proximal tubular portion, a first distal branch, and a second distal branch is provided. The assembly includes a housing that has a proximal end adapted to be coupled to the proximal tubular portion, a first flange adapted to be coupled to the first distal branch, and a second flange adapted to be coupled to the second distal branch. The housing has an inlet passage that has a first slot and a chamber extending from the inlet passage to the first and second flanges. A diverter member is coupled to the housing and is disposed in the chamber. The diverter member has a narrowed edge projecting proximally within the chamber. The assembly also includes a stylet that has a key coupled thereto. The key is adapted to cooperatively engage the first slot. The stylet may enter the inlet passage in a first preselected angular orientation and may be selectively wedged to either the first branch or the second branch when the stylet is thrust against the diverter member.

In accordance with another aspect of the present invention, a cardiac lead adapted to exchange electrical impulses with myocardial tissue, to be coupled to a cardiac stimulator, and to be manipulated spatially via a stylet is provided. The cardiac lead includes a proximal tubular portion adapted to be coupled proximally to the cardiac stimulator. A housing is coupled proximally to the proximal tubular portion. The housing has a first flange, a second flange, an inlet passage having a cross-section matching the stylet, and a chamber in communication with the inlet passage. A diverter member is coupled to the housing and is disposed in the chamber. The diverter member has a narrowed edge projecting proximally within the chamber. A first lead branch is coupled to the first flange and has a first tip coupled to the first lead branch distally. A second lead branch is coupled to the second flange and has a second tip coupled to the second lead branch distally. The stylet may engage the inlet passage enabling the stylet to enter the inlet passage in a first preselected angular orientation and to thereafter be selectively wedged to enter either the first branch or the second branch when the stylet is thrust against the diverter member.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
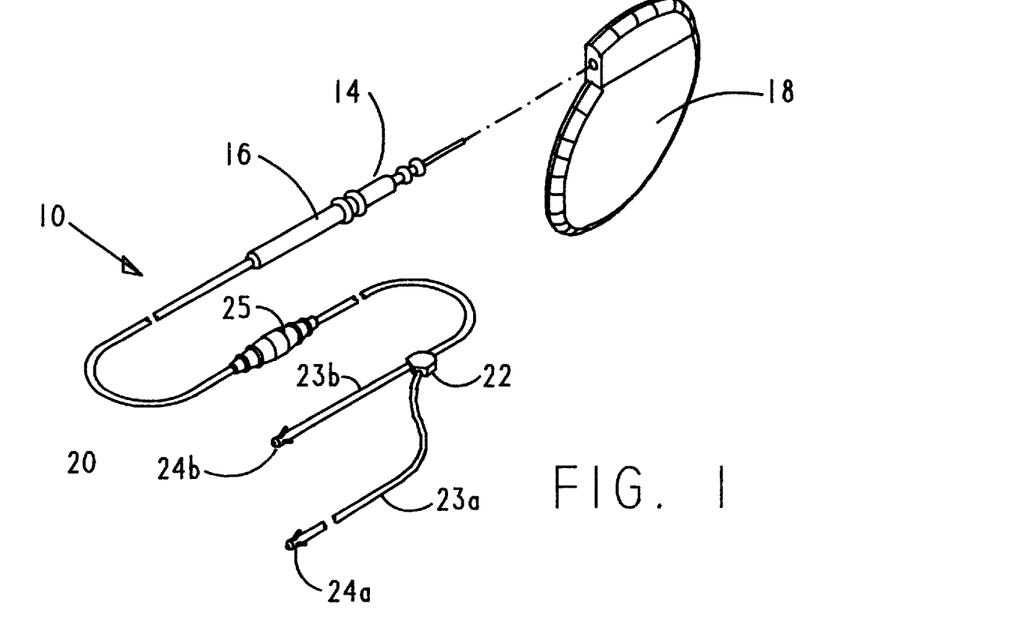
FIG. 1 is a pictorial view of an exemplary lead assembly in accordance with the present invention.
Figure 2:
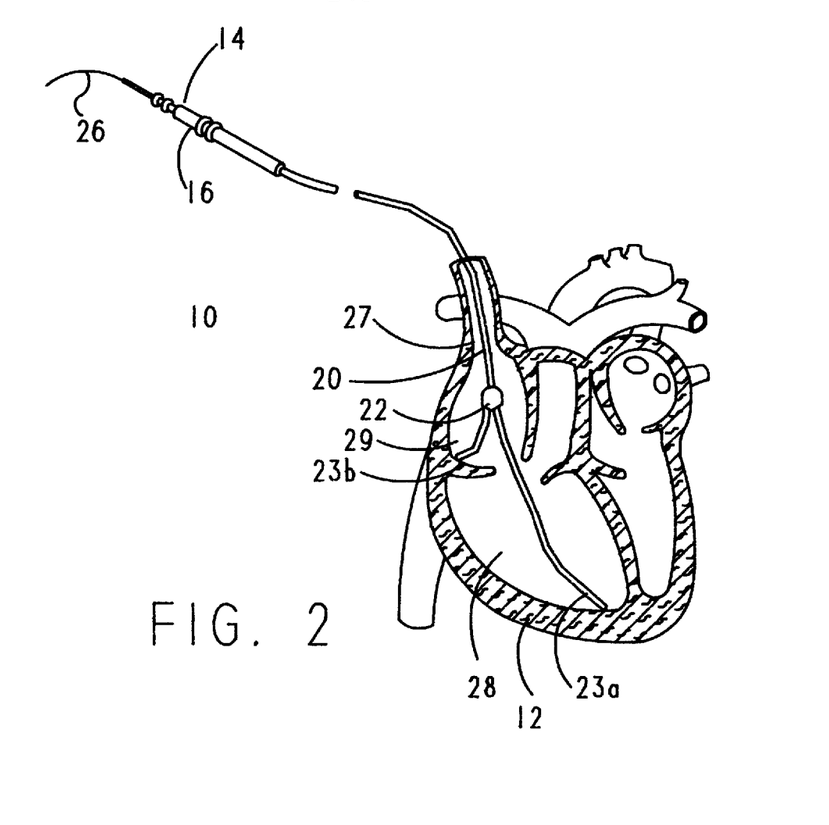
FIG. 2 is a partial cut away view of a heart showing implantation of the lead assembly in accordance with the present invention.

Turning now to the drawings, and in particular to FIGS. 1 and 2, there is shown an exemplary multiple distal branch lead assembly 10 which is adapted for transvenous implantation into a human heart 12. Reference numerals are generally reused in the figures where identical elements appear in more than one figure. The lead assembly 10 includes a proximal end 14 that has a connector 16 for electrical connection to a cardiac stimulator 18. The cardiac stimulator 18 may be a pacemaker, a cardioverter/defibrillator, or a sensing instrument. The lead assembly 10 includes an elongated proximal tubular portion 20 that extends distally from the connector 16. The distal end of the proximal tubular portion 20 is provided with a branch assembly 22 that is joined distally to two elongated distal lead branches 23a and 23b. The distal branches 23a and 23b are provided, respectively, with lead tips 24a and 24b that each function as electrodes for transferring electrical signals from and/or to the heart 12. The lead assembly 10 may also include a suture sleeve 25 that is disposed around the proximal tubular portion 20 to secure and protect the lead assembly 10 proximal to the site of transvenous entry.

In the initial phase of the implantation procedure for the lead assembly 10. an incision is made in the upper thoracic region above the areol 26 is introduced into the lead assembly 10. By manipulating the stylet 26, the distal branches 23a and 23b and the branch assembly 22 are introduced into one of the major veins leading to the heart, such as the subclavian vein or one of the internal jugular veins. The suture sleeve 25 is then sutured in place to secure the proximal end 14 of the lead assembly 10 proximal to the site of transvenous entry. After transvenous entry, the distal branches 23a and 23b and the branch assembly 22 are passed through the superior vena cava 27 and into the desired locations in the heart 12. For the purposes of this illustration, the particular endocardial locations are the right ventricle 28 and the right atrium 29.

Figure 3:
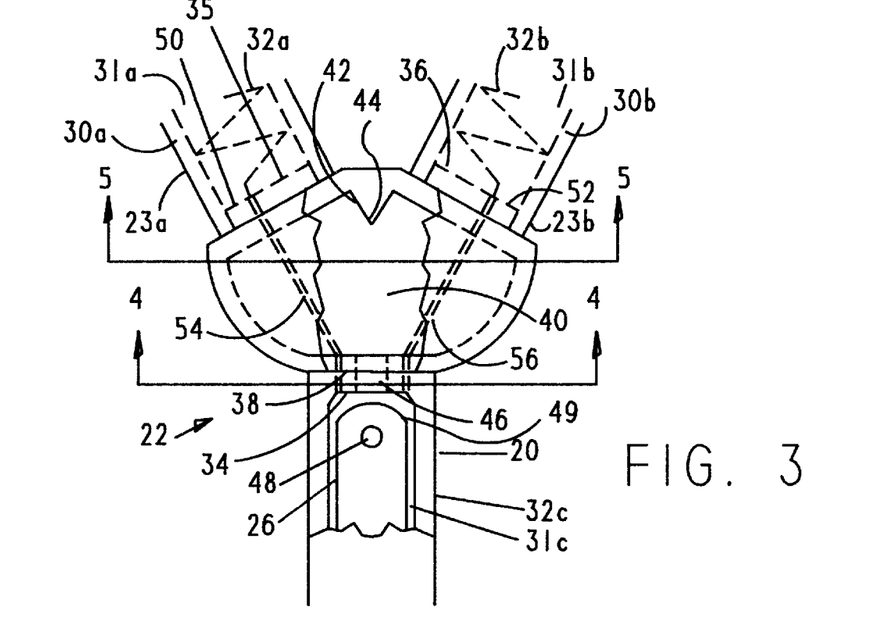
FIG. 3 is a plan view of the branch assembly of the lead assembly in accordance with the present invention.
Figure 4:
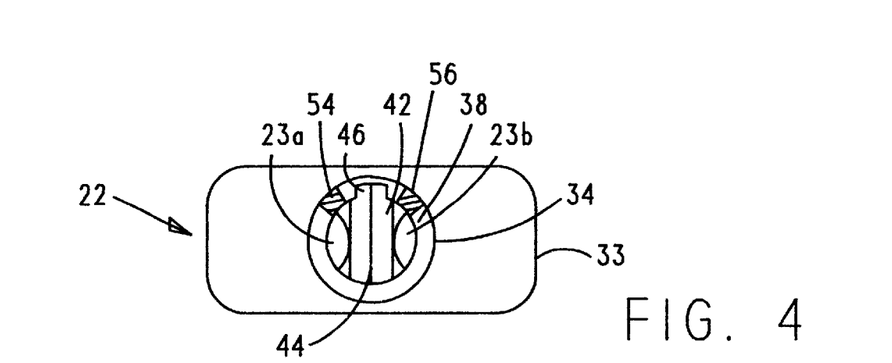
FIG. 4 is a cross-sectional view of FIG. 3 taken at section 4—4.
Figure 5:
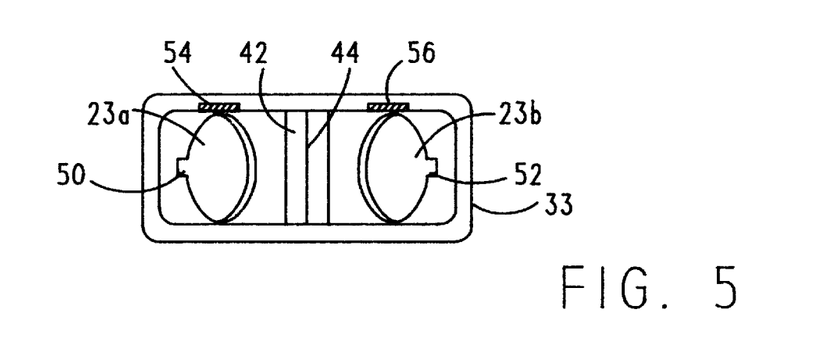
FIG. 5 is a cross-sectional view of FIG. 3 taken at section 5—5.

The detailed structure of the proximal tubular portion 20, the branch assembly 22, and the distal branches 23a and 23b may be understood by reference to FIGS. 3, 4, and 5. FIG. 3 is a plan view of the branch assembly 2. FIG. 4 is a sectional view of FIG. 3 taken at section 4—4, and FIG. 5 is a sectional view of FIG. 3 taken at section 5—5. The distal branches 23a and 23b and the proximal tubular portion 20 include respective tubular insulating sleeves 30a, 30b, and 30c, composed of a conventional biocompatible material such as polyurethane or silicone rubber. The sleeves 30a and 30b are secured proximally to the branch assembly 22 and distally to the respective lead tips 24a and 24b. The sleeves 30a, 30b, and 30c are secured to the branch assembly 22 and the sleeve 30c is secured to the connector 16 by any suitable biocompatible medical grade adhesive, such as Dow Medical Adhesive Silicone Type A. Each of the sleeves 30a, 30b, and 30c includes a respective coextensive lumen 31a, 31b, and 31c for receipt of the stylet 26. Conductor coils 32a, 32b, and 32c are respectively disposed in the lumens 31a, 31b, and 31c. The conductor coil 32b is connected proximally to the connector 16 and distally to the branch assembly 22, and consists of two or more separate conductor wires for respective electrical connection to the conductor coils 32a and 32b The conductor coils 32a and 32b are connected proximally to the branch assembly 22 and distally to their respective lead tips 24a and 24b. The conductor coils 32a, 32b, and 32c may be any of a variety of different types of conductor coils utilized in cardiac leads, such as, for example trifilar, bipolar coaxial, or Thinline™ (trademark of Sulzer Intermedics, Inc.).

The top of the branch assembly 22 is shown partially cut away in FIG.3 to reveal the interior of the branch assembly 22. The branch assembly 22 includes a housing 33 to which the proximal tubular portion 20 and the distal branches 23a and 23b are connected. The tubular portion 20 and the distal branches 23a and 23b are secured to the housing 33 by way of tubular flanges 34, 35, and 36 (34 is shown cut away, and flanges 35 and 36 are shown in phantom) using the adhesive discussed above. The housing 33 is provided with a generally proximally tapering profile to ease proximal movement of the branch assembly 22 and to lessen the risk of tissue injury in the event the branch assembly 22 must be moved proximally or removed. The housing 33 include an inlet passage 38 that provides access from the proximal tubular portion 20 into an internal chamber 40 that is open to the distal branches 23a and 23b. The housing 33 has a vertically disposed diverter member 42 that extends from the lower surface to the upper surface of the chamber 40 and has a tapered profile so that a narrowed edge 44 projects proximally. The narrowed edge 44 may have a width as narrow as a few thousandths of an inch. As discussed more fully below, the diverter member 42 functions to provide a wedge surface against which the stylet 26 may glide selectively into either the distal branch 23a or the distal branch 23b. The inlet passage 38 provides a pathway for the surgeon to advance the stylet 26 into the housing 33 and into engagement with the narrowed edge 44. The surgeon may selectively advance the stylet 26 into either of the branches 23a or 23b by wedging the stylet 26 to one side or the other of the diverter member 42. An appropriate pre-bend may be introduced into the stylet 26 to facilitate this wedging action. Entry into the selected branch may be verified by fluoroscopy or other imaging techniques. The particular geometry of the inlet passage 38 is a matter of design discretion, subject to the general requirement that the stylet 26 may readily pass therethrough.

Alternatively, the inlet passage 38 may be provided with a guide slot 46 that extends longitudinally from the flange 32 to the chamber 40 and is generally longitudinally aligned with the narrowed edge 44. In this case, the stylet 26 is provided with a radially projecting key 48 that is disposed near the tip 49 of the stylet 26 and is configured to cooperate with the slot 46. The inlet passage 38 is dimensioned to allow the stylet 26 to pass therethrough only when the radially projecting key 48 on the stylet is aligned with the guide slot 46. In this way, the stylet 26 will only pass into the chamber 40 in a preselected known angular orientation.

The flanges 35 and 36 are provided with respective guide slots 50 and 52 that extend longitudinally from the chamber 40 to the distal ends of the flanges 35 and 36. The guide slots 50 and 52 are dimensioned to enable sliding movement of the key 48 therethrough. As discussed more fully below, the guide slots 50 and 52 facilitate the selective sliding movement of the stylet 26 into either the distal branch 23a or the distal branch 23b.

To provide an electrical pathway between the conductor coils 32a and 32b and the conductor coil 32c, the housing 33 is provided with conductor traces 54 and 56 formed from any suitable biocompatible conducting metal, such as titanium, stainless steel, or similar materials. The conductor trace 54 extends from the proximal end of the flange 34 to the distal end of the flange 35, and the conductor trace 56 leads from the proximal end of the flange 34 to the distal end of the flange 36. The proximal portions of the conductor traces 54 and 56 form part of the peripheral surface of the flange 34. The mid-portions of the conductor traces 54 and 56 are either coupled to, or integrally formed with, the upper wall of the housing 33, and the distal portions of the conductor traces 54 and 56 form respective portions of the peripheral surfaces of the flanges 35 and 36. The respective conductor coils 32a, 32b, and 32c in the distal branches 23a, 23b, and the proximal portion 20 may be properly aligned with the corresponding proximal and distal ends of the conductor traces 54 and 56 at the time the tubular portion 20 and the distal branches 23a and 23b are secured to the housing 33.

The housing 33 may be fabricated from any conventional biocompatible electrically insulating material suitable for use in leads, such as polyurethane or Delrin®. It is anticipated that injection molding may be used to fabricate the housing 33. Accordingly, conductor traces 54 and 56 may be incorporated into the wall of the housing 33 during the injection molding process.

Figure 6:
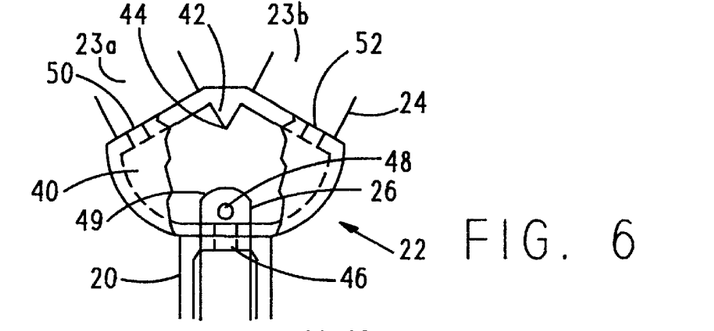
FIG. 6 is a plan view of the branch assembly of the present invention showing initial introduction of a stylet therein.

The operation of the branch assembly 22 may be understood by reference to FIGS. 6, 7, 8, and 9, which show, respectively, plan views of the branch assembly 22 at various stages during the selective manipulation of the stylet 26 therein. For simplicity of illustration, many of the structural details of the branch assembly 22 shown in previous figures are not shown in FIGS. 6–9, such as the conductor traces 54 and 56, and the flanges 34, 35, and 36. Assume for the purpose of this illustration that the surgeon has elected to manipulate the distal branch 23b. The stylet 26 is introduced into the proximal tubular portion 20 and advanced distally until the housing 33 is encountered as shown in FIG. 6. Imaging may be employed to verify the position of the stylet 26. If the stylet 26 is angularly positioned so that the key 48 is aligned with the guide slot 46, the stylet 26 will readily pass into the chamber 40. However, if the key 48 is not longitudinally aligned with the guide slot 46, stylet 26 will not advance further and the surgeon may then rotate the stylet 26 until the key 48 and the guide slot 46 are aligned and the stylet 26 freely passes into the chamber 40. In either case, the stylet 26 will pass into the chamber in a known preselected angular orientation.

Figure 7:
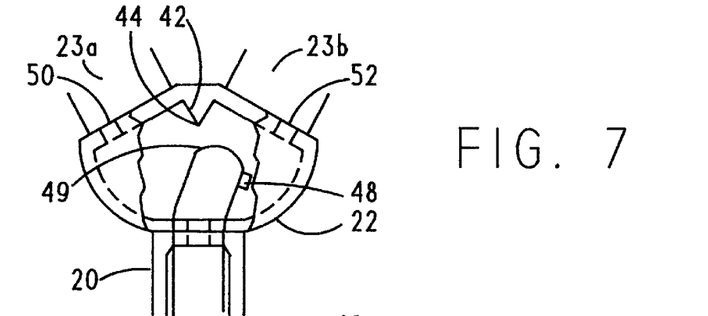
FIG. 7 is a plan view of the branch assembly of the present invention showing further introduction of a stylet therein.
Figure 8:
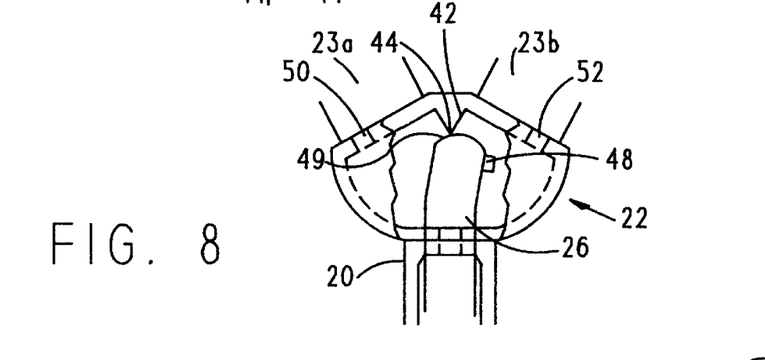
FIG. 8 is a plan view of the branch assembly of the present invention showing introduction of a stylet therein and engagement with the diverter member.

After the key has cleared the slot 46, the stylet 26 is rotated clockwise so that the key 46 projects toward the guide slot 52 as shown in FIG. 7. After the stylet 26 is rotated toward the distal branch 23b, the stylet 26 is advanced longitudinally until the tip 49 engages the diverter member 42. Because the width of the narrowed edge 44 is quite small in relation to the diameter of the stylet 26, the tip 49 may wedge to either side of the diverter member 42 upon engagement with the narrowed edge 44. To ensure that the tip 49 is wedged to the desired distal branch, in this case 23b, the tip 49 should be either provided with a pre-bend or moved laterally just prior to engagement with the narrowed edge 44 so that the tip 49 engages the narrowed edge 44 slightly off-center toward the distal branch 23b as shown in FIG. 8. A pre-bend may be introduced into the stylet 26 by hand prior to insertion such that the larger radius of curvature of the bend falls on the opposite side of the stylet 26 from the key 48. The bend should be made somewhere within the portion of the distal end of the stylet 26 that is disposed within the housing 22 just prior to engagement with the narrowed edge 44 as shown in FIG. 8.

Figure 9:
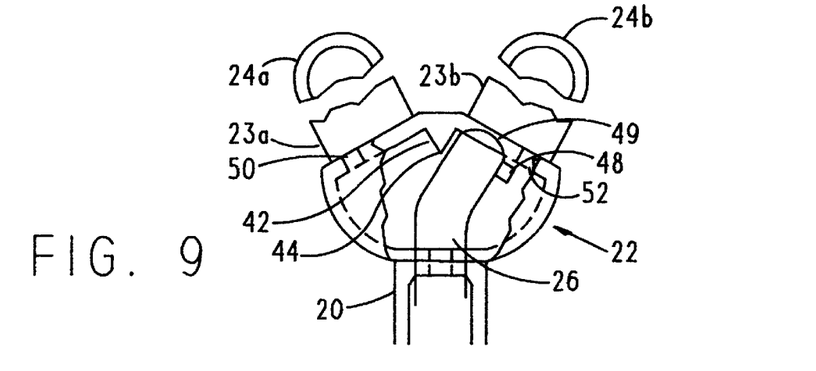
FIG. 9 is a plan view of the branch assembly of the present invention showing introduction of a stylet therein and passage of the stylet into one of the distal branches of the lead assembly.

As shown in FIG. 9, at the time the tip 49 enters the distal branch 23b, the key 48 should slidably engage the guide slot 52. After entering the distal branch 23b, the stylet 26 may be advanced longitudinally as necessary to selectively place the lead tip 24b. Due to the extremely small width of the narrowed edge 44 and the relatively small diameter of the stylet 26, it is anticipated that the amount of lateral movement or pre-bend of the tip 49 necessary to achieve the desired off-center engagement will be relatively small, perhaps on the order of a few thousandths of an inch. In the embodiment shown in FIGS. 6, 7, 8, and 9, the off-center engagement is achieved via a pre-bend in the stylet 26. As discussed below other mechanical schemes for achieving the required lateral movement of the tip 49 are possible.

The diameter of the flange 36 in conjunction with the guide slot 52 ensure that the tip 49 will only be received in the distal branch 23b in a preselected known angular orientation. Thus, the surgeon may know with confidence that by rotating the stylet 26 through a particular angle, and sensing a tactile longitudinal movement of the stylet 26, the stylet 26 has advanced into the desired distal branch. After passing the flange 36, the stylet 26 may return to the original angular position shown in FIG. 6. At this point, the key 48 will prevent withdrawal of the stylet 26, enabling the surgeon to apply tension on the branch assembly 22 to effect movement or removal of the lead assembly 10, if necessary.

If the tip 49 is inadvertently moved laterally to the wrong side of the diverter member 42 for a given distal branch, the misalignment should be readily detected by tactile response, and possibly by imaging, since any attempt to rotate the stylet 26 in the required direction will simply result in the key 48 binding against the diverter member 42.

Movement of the stylet 26 into the distal branch 23a, either initially or after manipulation of the distal branch 23b, may be accomplished by introducing the stylet 26 into the housing 33 as described above and then rotating the stylet 26 counterclockwise and advancing the stylet 26 longitudinally as described above to move the tip 49 into the branch 23a. In this regard, both distal branches 23a and 23b may be spatially manipulated using a single stylet and a single lumen 31c proximal to the distal branches 23a and 23b.

Figure 10:
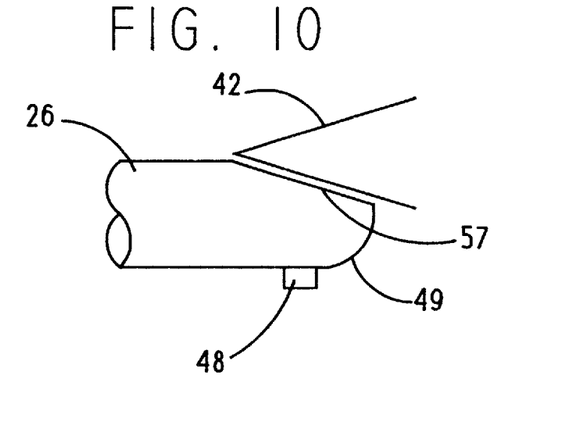
FIG. 10 is a side view of an alternative stylet design.

The particular configuration of the stylet 26 and the key 48 are a matter of design discretion and the skilled artisan will appreciate that a variety of geometries are permissible, subject to the general requirement that the stylet 26 may readily pass through the inlet passage 38 and the flanges 35 and 36. The key 48 may be formed integrally with the stylet 26 by machining or it may be attached as a separate piece by spot welding. The key 48 may be designed to shear or otherwise break away from the stylet to enable the surgeon to remove the stylet 26 in the event stylet 26 becomes inadvertently stuck in one of the distal branches 23a or 23b or the branch assembly 22. In addition, as shown in FIG. 10, the tip 49 may be provided with a beveled surface 57 to aid the wedging engagement between the tip 49 and the diverter member 42. A Teflon® coating may also be applied to the stylet 26 to further facilitate its relative sliding movement throughout the lead assembly 10.

Note that the foregoing embodiment utilized distal branches 23a and 23b having passively fixated tips 24a and 24b. However, active fixation may be employed to secure the tips 24a and 24b to the myocardium. One or both of the tips 24a or 24b may employ an active screw-in fixation mechanism. If only one tip employs active fixation, the manipulation of the distal branches 23a and 23b may be accomplished as discussed above, although the distal branch that has the screw-in tip should be placed prior to the placement of the passively fixated tip if the screw-in tip cannot rotate independently of the lead body. This is due to the fact that the fixation of the screw-in tip may involve a twisting of the lead assembly 10, which might result in an undesirable dislodging of the passively fixated tip.

Figure 11:
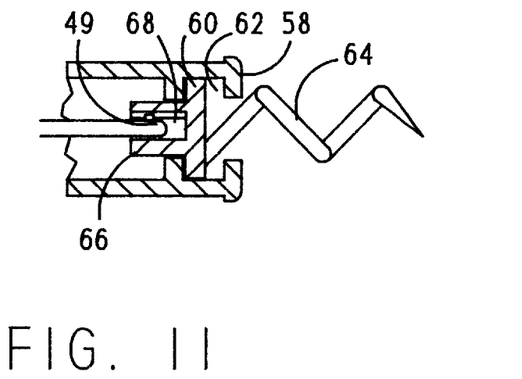
FIG. 11 is a cross-sectional view of an alternative embodiment of a lead tip in accordance with the present invention.
Figure 12:
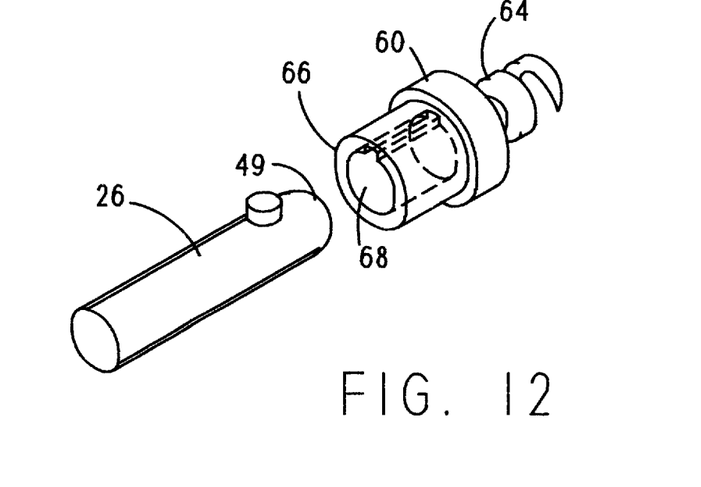
FIG. 12 is a pictorial view of the swivel member shown in FIG. 11.

If both of the distal branches 23a and 23b employ a screw-in active fixation tip, the skilled artisan will appreciate that the twist imposed upon the lead assembly 10 when the second of the two distal branches is attached may undesirably dislodge the first placed distal branch from the myocardium and cause the distal branches 23a and 23b to become raveled. A solution to this potential problem is shown in FIG. 11, which is a sectional view of a distal tip 58 that utilizes active screw-in fixation and may be used for both of the distal branches 23a and 23b disclosed above. The tip 58 incorporates a swivel 60 that is rotatably disposed in a cylindrical chamber 62 in the tip 58. FIG. 12 shows a pictorial view of the swivel 60 from the tip 58. A screw-in hook 64 is coupled to and projects from the distal end of the swivel 60. The proximal end of the swivel 60 includes a reduced diameter cylindrical portion 66 that has a longitudinally disposed bore 68 that is keyed to receive the stylet tip 49 in much the same fashion as the guide slots 50 and 52 disclosed above. In operation, the tip 49 is advanced into the bore 68 and the stylet 26 rotated clockwise or counterclockwise depending upon the twist of the hook 64. Because the swivel 60 is free to rotate independent of the tip 58, torque applied from the stylet 26 is not transmitted to the tip 58. As a result, the tip 58 will not twist. In this way, fixation of the tip 58 will not inadvertently dislodge a previously attached screw-in tip.

Figure 13:
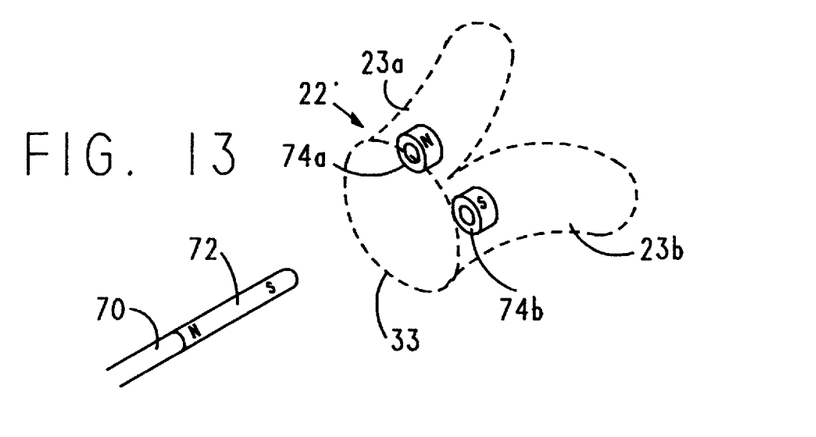
FIG. 13 is a pictorial view of an alternate embodiment of the lead assembly incorporating a permanent magnet stylet steering mechanism in accordance with the present invention.

As noted above, there are many mechanical mechanisms suitable for initiating the desired lateral movement of the stylet tip 49 relative to the diverter member 42 and for providing assurance that the stylet 26 is advanced into the desired branch. For example, FIG. 13 shows a highly simplified pictorial of an alternative embodiment of the branch assembly 22' where the housing 33 is shown in phantom for simplicity of illustration. A stylet 70 includes a permanent magnet 72 coupled at a distal end. The permanent magnet 72 is coupled to the stylet 70 so that the south pole of the magnet 72 projects distally. The distal 23a and 23b are respectively provided with annular permanent magnets 74a and 74b. The magnet 74a is disposed in the distal branch 23a so that its north magnetic pole projects proximally. Conversely, the magnet 74b is disposed in the distal branch 23b so that its south magnetic pole project proximally. As the stylet 70 is advanced into the housing 33, the south pole on the magnet 74 repels the south pole on the distal end of the magnet 72 and the north pole on the magnet 74a attracts the south pole on the magnet 72. The combined repulsion and attraction move the stylet 70 laterally toward the magnet 74a, ensuring that the stylet 70 enters the branch 23a as desired. A separate stylet (not shown) having a magnet with reverse polarity may then be used to advance into the distal branch 23b.

Figure 14:
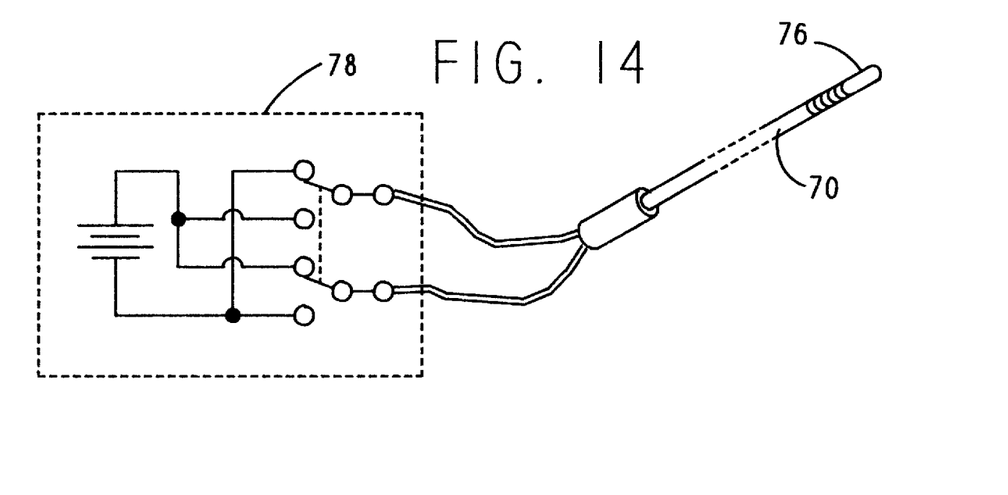
FIG. 14 is a pictorial view of an alternate embodiment of the lead assembly incorporating an electromagnet stylet steering mechanism in accordance with the present invention.

FIG. 14 discloses another alternative arrangement. The stylet 70 may be fitted with an electromagnet 76 instead of the permanent magnet 72 shown in FIG. 13. The stylet 70 is removably connected to an external DC power source indicated by the dashed box 78. The polarity of the tip of the electromagnet 76 may be varied by controlling the direction of the current at the magnet 76. In this regard, the polarity of the tip of the electromagnet 76 may be set to either attract or repel the permanent magnets 74a and 74b shown in FIG. 13. After the stylet 70 is passed through one or the other of the permanent magnets 74a or 74b, the power source 78 may be unplugged from the stylet 70 to facilitate easier handling of the stylet 70.

Figure 15:
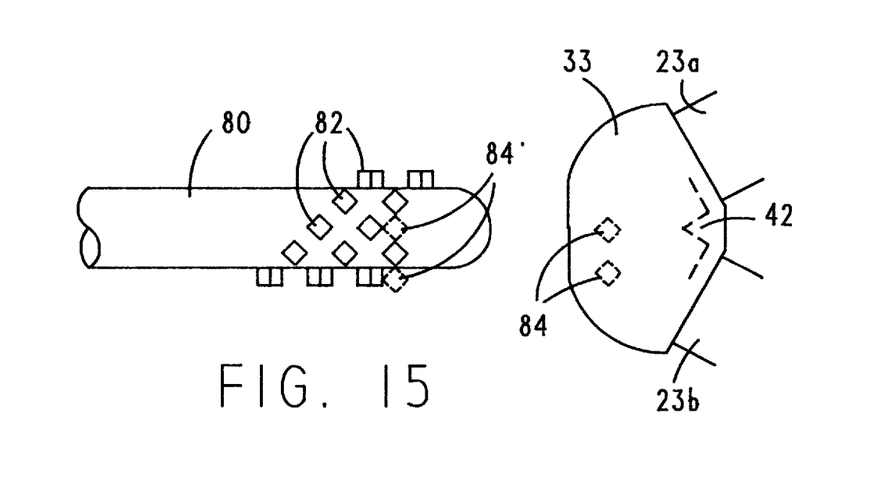
FIG. 15 is a plan view of an alternate embodiment of the lead assembly incorporating a bidirectional thread stylet steering mechanism.

Another alternative for initiating a lateral movement of a stylet relative to the diverter member 42 is shown in FIG. 15. A stylet 80 is provided with a plurality of external bidirectional threads 82. A mating set of bidirectional internal threads 84 is provided inside the housing 33. The internal threads 84 are positioned in the housing 33 so that when the stylet 80 is introduced into the housing 33, and advanced until the external threads 82 engage the internal threads 84, the internal threads 84 will occupy the spatial position relative to the external threads 82 shown by the dashed diamonds 84'. Subsequent to initial engagement of the external threads 82 and the internal threads 84, clockwise rotation of the stylet 80 will cause a slight lateral movement of the stylet 80 toward the distal branch 23b. Conversely, counterclockwise rotation of the stylet 80 will result in a slight lateral movement of the stylet 80 in the direction of the distal branch 23a. In addition to providing a mechanism for achieving the desired lateral movement of the stylet 80 relative to the diverter member 42, the cooperating external threads 82 and the internal threads 84 provide a means for temporarily securing the stylet 80 to the housing 33. This temporary engagement will enable the surgeon to apply tension to the stylet 80 to facilitate movement or removal of the lead assembly 10, if necessary.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A branch assembly for a cardiac lead, said cardiac lead having a proximal tubular portion, a first distal branch, and a second distal branch, said first and second distal branches being adapted to be spatially manipulated by a stylet, comprising:

a housing having a proximal end adapted to be coupled to said proximal tubular portion, a first flange adapted to be coupled to said first distal branch, a second flange adapted to be coupled to said second distal branch, an inlet passage, and a chamber extending from said inlet passage to said first and second branches; and a diverter member coupled to said housing and being disposed in said chamber, said diverter member having a narrowed edge projecting proximally within said chamber whereby said stylet may be selectively wedged to either said first branch or said second branch when said stylet is thrust against said diverter member.

2. The branch assembly of claim 1, wherein said inlet passage is adapted to receive a stylet having a key coupled distally thereon, said inlet passage has a first slot adapted to receive said key, said first flange has a second slot adapted to receive said key, and said second flange has a third slot adapted to receive said key such that said first slot enables said stylet to be received in a first preselectecd angular orientation, said second slot enables said stylet to be received in a second preselected angular orientation in said first branch and said third slot enables said stylet to be received in a third preselected orientation in said second branch.

3. The branch assembly of claim 1, wherein said inlet passage is adapted to receive a stylet having a first set of external bidirectional threads and said housing has a second set of internal bidirectional threads, said first set of external threads and said second set of internal threads being cooperating such that, when said sets of external and internal threads are engaged and said stylet is rotated clockwise, said stylet moves laterally in a first direction, and when said stylet is rotated counterclockwise said stylet moves laterally in a direction opposite to said first direction.

4. The branch assembly of claim 1, wherein said inlet passage is adapted to receive a stylet having a first magnet having a first magnetic pole disposed distally, said first branch having second magnet having a second magnetic pole disposed proximally, said second magnetic pole being magnetically opposite to said first magnetic pole, and said second branch having a third magnet having said first magnetic pole disposed proximally, whereby said first magnet and said second magnet attract to urge said stylet toward said first branch.

5. The branch assembly of claim 1, wherein said inlet passage is adapted to receive a stylet having a first magnet having a first magnetic pole disposed distally, said first branch having a second magnet having said first magnetic pole disposed proximally, and said second branch having a third magnet having a second magnetic pole disposed proximally, said second magnetic pole being magnetically opposite to said first magnetic pole, whereby said first magnet and said third magnet attract to urge said stylet toward said second branch.

6. An assembly for spatially manipulating the branches of a multiple branch cardiac lead, said cardiac lead having a proximal tubular portion, a first distal branch, and a second distal branch, comprising:

a housing having a proximal end adapted to be coupled to said proximal tubular portion, a first flange adapted to be coupled to said first distal branch, a second flange adapted to be coupled to said second distal branch, an inlet passage, a chamber extending from said inlet passage to said first and second flanges, and a diverter member coupled to said housing and being disposed in said chamber, said diverter member having a narrowed edge projecting proximally within said chamber;

a stylet having a cross-section matching said inlet passage and removably inserted in said inlet passage; and whereby said stylet may enter said inlet passage and may be selectively wedged to either said first branch or said second branch when said stylet is thrust against said diverter member.

7. The assembly of claim 6, wherein said stylet has a key coupled thereto, said inlet passage has a first slot adapted to receive said key, said first flange has a second slot adapted to receive said key and said second flange has a third slot adapted to receive said key such that said first slot enables said stylet to be received in said inlet passage in a first preselected angular orientation, said second slot enables said stylet to be received in said first flange in a second preselected angular orientation and said third slot enables said stylet to be received in said second flange in a third preselected angular orientation.

8. The assembly of claim 6, wherein said stylet has a first set of external bi-directional threads and said housing has a second set of internal bi-directional threads, said first set of external threads and said second set of internal threads being cooperating such that, when said sets of external and internal threads are engaged and said stylet is rotated clockwise, said stylet moves laterally in a first direction, and when said stylet is rotated counterclockwise said stylet moves laterally in a direction opposite to said first direction.

9. The assembly of claim 6, wherein said stylet has a first magnet having a first magnetic pole disposed distally, said first branch having a second magnet having a second magnetic pole disposed proximally, said second magnetic pole being magnetically opposite to said first magnetic pole, and said second branch having a third magnet having said first magnetic pole disposed proximally, whereby said first magnet and said second magnet attract to urge said stylet toward said first branch.

10. The assembly of claim 6, wherein said stylet has a first magnet having first magnetic pole disposed distally, said first branch having a second magnet having said first magnetic pole disposed proximally, and said second branch having a third magnet having a second magnetic pole disposed proximally, said second magnetic pole being magnetically opposite to said first magnetic pole, whereby said first magnet and said third magnet attract to urge said stylet toward said second branch.

11. A cardiac lead adapted to exchange electrical impulses with myocardial tissue and adapted to be manipulated spatially via a stylet, comprising:

a proximal tubular portion adapted to be coupled proximally to said cardiac stimulator;

a housing coupled proximally to said proximal tubular portion, said housing having a first flange, a second flange, an inlet passage, a chamber in communication with said inlet passage, and a diverter member coupled to said housing and being disposed in said chamber, said diverter member having a narrowed edge projecting proximally within said chamber;

a first lead branch coupled to said first branch and having a first electrode coupled to said first lead branch distally;

a second lead branch coupled to said second branch and having a second electrode coupled to said second lead branch distally; and whereby said stylet may engage said inlet passage enabling said stylet to thereafter be selectively wedged to enter either said first branch or said second branch when said stylet is thrust against said diverter member.

12. The branch assembly of claim 11, wherein said stylet has a key, said inlet passage has a first slot adapted to receive said key, said first flange has a second slot adapted to receive said key, and said second flange has a third slot adapted to receive said key such that said first slot enables said stylet to be received in a first preselected angular orientation, said second slot enables said stylet to be received in a second preselected angular orientation in said first flange and said third slot enables said stylet to be received in a third preselected orientation in said second flange.

13. The branch assembly of claim 11, wherein said stylet has a first set of external bi-directional threads and said housing has a second set of internal bi-directional threads, said first set of external threads and said second set of internal threads being cooperating such that, when said sets of external and internal threads are engaged and said stylet is rotated clockwise, said stylet moves laterally in a first direction, and when said stylet is rotated counterclockwise said stylet moves laterally in a direction opposite to said first direction.

14. The branch assembly of claim 11, wherein said stylet has a first magnet having a first magnetic pole disposed distally, said first branch having a second magnet having a second magnetic pole disposed proximally, said second magnetic pole being magnetically opposite to said first magnetic pole, and said second branch having a third magnet having said first magnetic pole disposed proximally, whereby said first magnet and said second magnet attract to urge said stylet toward said first branch.

15. The branch assembly of claim 11, wherein said stylet has a first magnet having a first magnetic pole disposed distally, said first branch having a second magnet having said first magnetic pole disposed proximally, and said second branch having a third magnet having a second magnetic pole disposed proximally, said second magnetic pole being magnetically opposite to said first magnetic pole, whereby said first magnet and said third magnet attract to urge said stylet toward said second branch.

16. The cardiac lead of claim 11, wherein each of said first and said second electrodes comprises:
 a tubular housing; and
 a swivel member coupled to said tubular housing and being operable to rotate relative to said tubular housing, said swivel having a distally projecting screw for penetrating said myocardial tissue and an opening for receiving said stylet, said opening having a fourth slot for engaging said key whereby said stylet may be inserted into said opening and turned to rotate said screw.

* * * * *